US012268491B2

(12) United States Patent
Avery et al.

(10) Patent No.: US 12,268,491 B2
(45) Date of Patent: Apr. 8, 2025

(54) SENSOR SYSTEM FOR DETERMINING THE SHAPE OF A DEFORMABLE STRUCTURE

(71) Applicant: IMPERIAL COLLEGE INNOVATIONS LIMITED, London (GB)

(72) Inventors: James Avery, Beckenham (GB); Mark Runciman, London (GB); George Mylonas, London (GB)

(73) Assignee: IMPERIAL COLLEGE INNOVATIONS LIMITED, London (GB)

( * ) Notice: Subject to any disclaimer, the term of this patent is extended or adjusted under 35 U.S.C. 154(b) by 645 days.

(21) Appl. No.: 17/416,959

(22) PCT Filed: Dec. 20, 2019

(86) PCT No.: PCT/GB2019/053657
§ 371 (c)(1),
(2) Date: Jun. 21, 2021

(87) PCT Pub. No.: WO2020/128509
PCT Pub. Date: Jun. 25, 2020

(65) Prior Publication Data
US 2022/0079466 A1 Mar. 17, 2022

(30) Foreign Application Priority Data
Dec. 21, 2018 (GB) ...................................... 1821129

(51) Int. Cl.
*G01B 7/16* (2006.01)
*A61B 5/06* (2006.01)
(Continued)

(52) U.S. Cl.
CPC .............. *A61B 5/063* (2013.01); *A61B 34/30* (2016.02); *G01B 7/16* (2013.01); *A61B 5/0536* (2013.01)

(58) Field of Classification Search
CPC ... G01B 7/16; G01B 7/18; G01B 7/28; G01B 7/287; A61B 2034/2061; A61B 5/063; A61B 5/0536; A61B 34/30; G01L 1/142
See application file for complete search history.

(56) References Cited

U.S. PATENT DOCUMENTS 5,042,164 A * 8/1991 Eppinger ............... G01B 7/287
33/561.2
5,272,624 A * 12/1993 Gisser .................. A61B 5/0536
600/393
(Continued)

FOREIGN PATENT DOCUMENTS

KR 20120012758 A * 2/2012
WO 8909564 10/1989
(Continued)

OTHER PUBLICATIONS

Abidi, et al., "Highly dexterous 2-module soft robot for intra-organ navigation in minimally invasive surgery," Int. J. Med. Robot. Comput. Assist. Surg., 14 (1): 1-9 (2018).
(Continued)

Primary Examiner — Lee E Rodak
Assistant Examiner — Demetrius R Pretlow
(74) Attorney, Agent, or Firm — PABST PATENT GROUP LLP

(57) ABSTRACT

A sensor system comprising: a deformable structure; a plurality of electrodes operably connectable to the deformable structure; an electrical conductor operably connected to the deformable structure and electrically couplable to each of the electrodes; a current source connectable to predetermined electrodes; a current injector for injecting current
(Continued)

from the current source through predetermined electrodes; a voltage recorder for recording the voltage between predetermined pairs of electrodes; and an analyser for analysing voltage recordings to thereby determine the shape of the deformable structure.

14 Claims, 7 Drawing Sheets

(51) Int. Cl.
*A61B 34/30* (2016.01)
*A61B 5/0536* (2021.01)

(56) References Cited

U.S. PATENT DOCUMENTS

| | | | | |
|---|---|---|---|---|
| 5,760,530 | A * | 6/1998 | Kolesar | H10N 39/00 |
| | | | | 310/317 |
| 6,501,984 | B1 * | 12/2002 | Church | A61B 5/0536 |
| | | | | 600/547 |
| 9,080,918 | B2 * | 7/2015 | Fishel | G01L 5/228 |
| 11,334,198 | B2 * | 5/2022 | Ramani | G06F 3/044 |
| 2002/0106681 | A1 * | 8/2002 | Wexler | G01N 27/041 |
| | | | | 702/19 |
| 2002/0188174 | A1 * | 12/2002 | Aizawa | A61B 5/064 |
| | | | | 600/109 |
| 2003/0204149 | A1 * | 10/2003 | Streng | A61B 5/391 |
| | | | | 600/546 |
| 2004/0167426 | A1 * | 8/2004 | Vantrappen | A61B 5/42 |
| | | | | 600/560 |
| 2005/0272971 | A1 * | 12/2005 | Ohnishi | A61B 1/0005 |
| | | | | 600/101 |
| 2006/0152885 | A1 * | 7/2006 | Hewit | A61B 5/1076 |
| | | | | 361/283.1 |
| 2009/0264752 | A1 * | 10/2009 | Markowitz | A61B 34/20 |
| | | | | 600/425 |
| 2009/0293664 | A1 | 12/2009 | Aabloo | |
| 2010/0049450 | A1 * | 2/2010 | Nagakubo | G01L 5/228 |
| | | | | 702/41 |
| 2010/0168836 | A1 * | 7/2010 | Kassab | A61F 2/2433 |
| | | | | 623/1.11 |
| 2011/0094306 | A1 * | 4/2011 | Bratkovski | G01L 5/228 |
| | | | | 73/849 |
| 2011/0254572 | A1 * | 10/2011 | Yamaguchi | G01B 7/023 |
| | | | | 324/688 |
| 2011/0307214 | A1 * | 12/2011 | Saitou | G01B 7/16 |
| | | | | 702/155 |
| 2012/0116386 | A1 * | 5/2012 | Govari | A61B 18/1492 |
| | | | | 606/41 |
| 2012/0197097 | A1 * | 8/2012 | Chan | A61B 90/06 |
| | | | | 600/478 |
| 2013/0109962 | A1 * | 5/2013 | Uutela | A61B 5/0536 |
| | | | | 600/476 |
| 2013/0255396 | A1 * | 10/2013 | Cho | G01N 3/08 |
| | | | | 73/789 |
| 2014/0208731 | A1 | 7/2014 | Shepherd | |
| 2014/0365009 | A1 * | 12/2014 | Wettels | B25J 19/023 |
| | | | | 700/258 |
| 2015/0366485 | A1 * | 12/2015 | Kassab | A61B 5/6886 |
| | | | | 600/481 |
| 2016/0066794 | A1 * | 3/2016 | Klinder | A61B 5/02028 |
| | | | | 600/424 |
| 2016/0242673 | A1 * | 8/2016 | Grychtol | G09B 23/30 |
| 2016/0302690 | A1 * | 10/2016 | Nebuya | A61B 5/6823 |
| 2017/0010130 | A1 * | 1/2017 | Xu | G06F 3/014 |
| 2018/0216969 | A1 * | 8/2018 | Ikeda | G01L 1/144 |
| 2019/0076085 | A1 * | 3/2019 | Woo | A61B 5/4818 |
| 2019/0133528 | A1 * | 5/2019 | Kassab | A61F 2/2496 |
| 2019/0217083 | A1 * | 7/2019 | Raspopovic | A61B 5/24 |
| 2019/0254649 | A1 * | 8/2019 | Walters | A61B 1/05 |
| 2019/0307359 | A1 * | 10/2019 | Smela | A61B 5/6843 |
| 2019/0328252 | A1 * | 10/2019 | Myllykangas | H05K 1/09 |
| 2020/0138525 | A1 * | 5/2020 | Hill | A61B 5/6858 |
| 2020/0229866 | A1 * | 7/2020 | Harlev | A61B 18/1492 |
| 2020/0405384 | A1 * | 12/2020 | Panescu | A61B 18/14 |

FOREIGN PATENT DOCUMENTS

| | | |
|---|---|---|
| WO | 2008003266 | 1/2008 |
| WO | 2009124209 | 10/2009 |
| WO | 2016029143 | 2/2016 |
| WO | 2019108861 | 6/2019 |

OTHER PUBLICATIONS

Ad-Tech Medical <https://adtechmedical.com/> accessed Jan. 25, 2022.
Aristovich, et al., "A method for reconstructing tomographic images of evoked neural activity with electrical impedance tomography using intracranial planar arrays", Physiol. Meas., 35:1095-1109 (2014).
Lee, et al., "Soft Nanocomposite Based Multipoint, Multi-directional Strain Mapping Sensor Using Anisotropic Electrical Impedance Tomography", Scientific Reports, 7(39837): 1-10 (2017).
Niiyama, et al., "Pouch Motors: Printable/inflatable soft actuators for robotics," Proc.—2014 IEEE Int. Conf. Robot. Autom., 6332-6337, 2014.
Ogura, et al., "Micro pneumatic curling actuator—Nematode actuator—," 2008 IEEE Int. Conf. Robot. Biomimetics, 462-467 (2009).
Sareh, et al., "Bio-Inspired Tactile Sensor Sleeve for Surgical Soft Manipulators", http://researchonline.rca.ac.uk/ 3384/1/ICRA14_0925_FI4.pdf (2014).
Shi, et al., "Shape sensing techniques for continuum robots in minimally invasive surgery: A survey," IEEE Trans. Biomed. Eng., 64 (8): 1665-1678 (2017).
SwissTom Pioneer set, <http://www.swisstom.com/en/products/pioneer-set>, accessed Jan. 25, 2022.
Visentin, et al., "A Deformable Smart Skin for Continuous Sensing Based on Electrical Impedance Tomography" Sensors, 16(1928): 1-21 (2016).
Vrielink, et al., "A new robotic surgical system for GI surgery", 2018 IEEE Int. Conf. Robot. Autom. (2017).
International Search Report for PCT/GB2019/053657 dated Apr. 2, 2020.
Shah, et al., "Magnetic imaging of colonoscopy: An audit of looping, accuracy and ancillary maneuvers," Gastrointest. Endosc., 52(1): 1-8 (2000).

* cited by examiner

Figure 3a
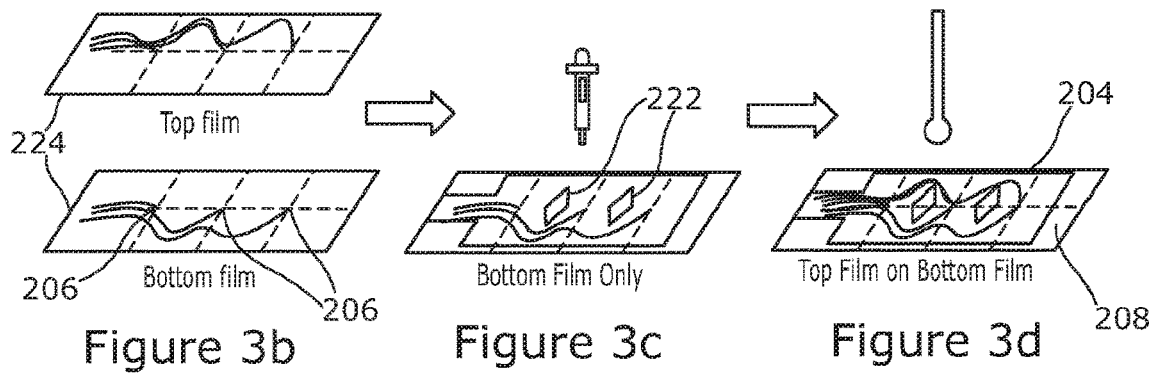
Figure 3b    Figure 3c    Figure 3d
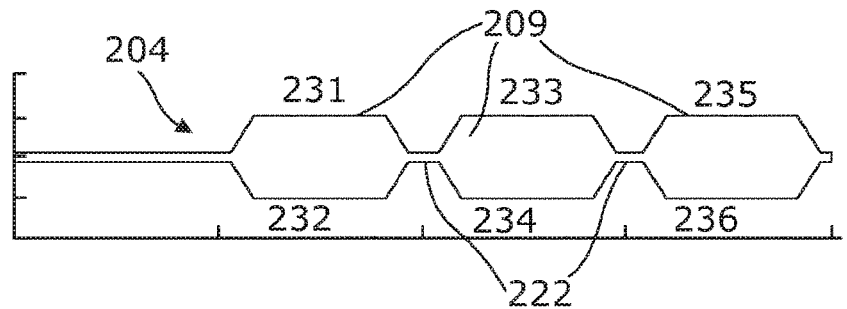
Figure 4a
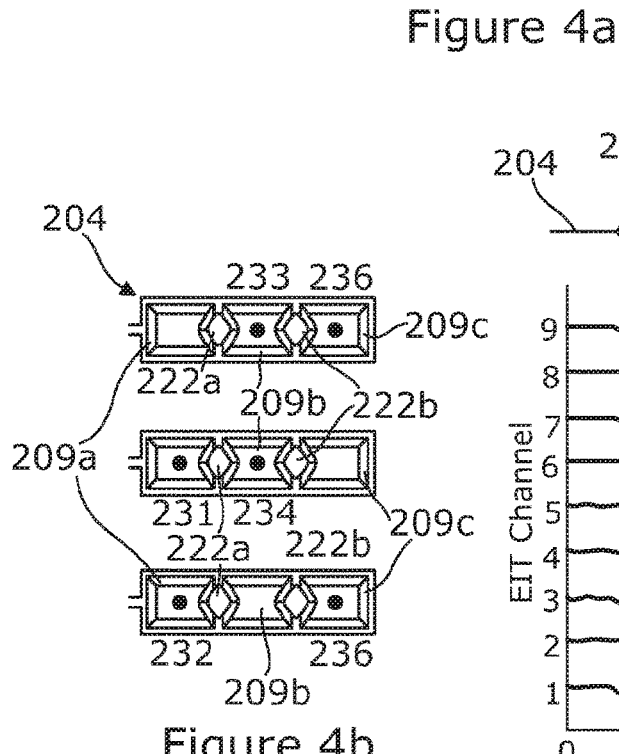
Figure 4b
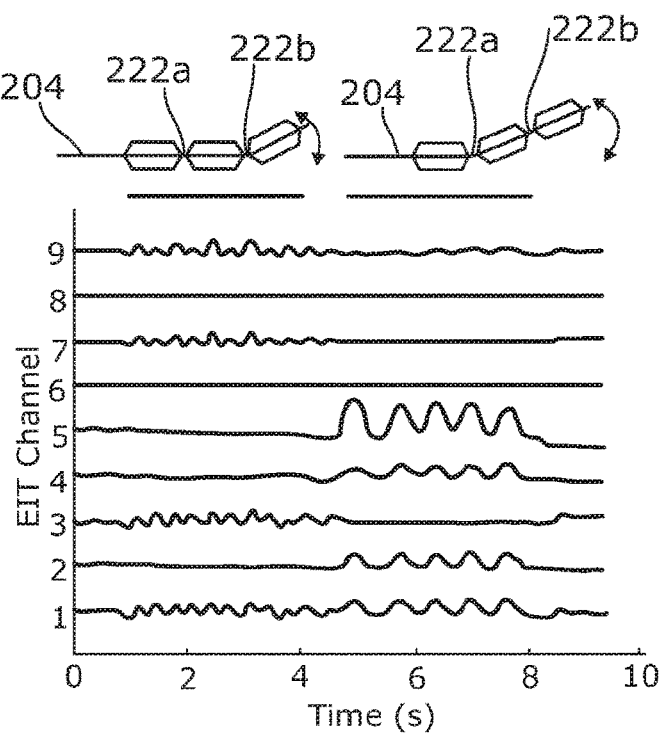
Figure 4c

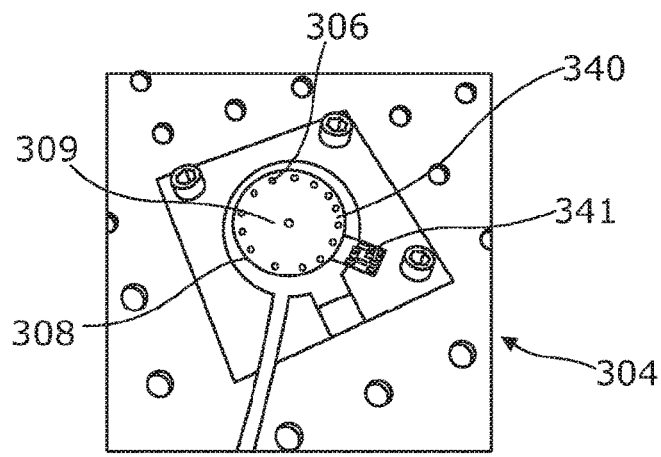
Figure 5
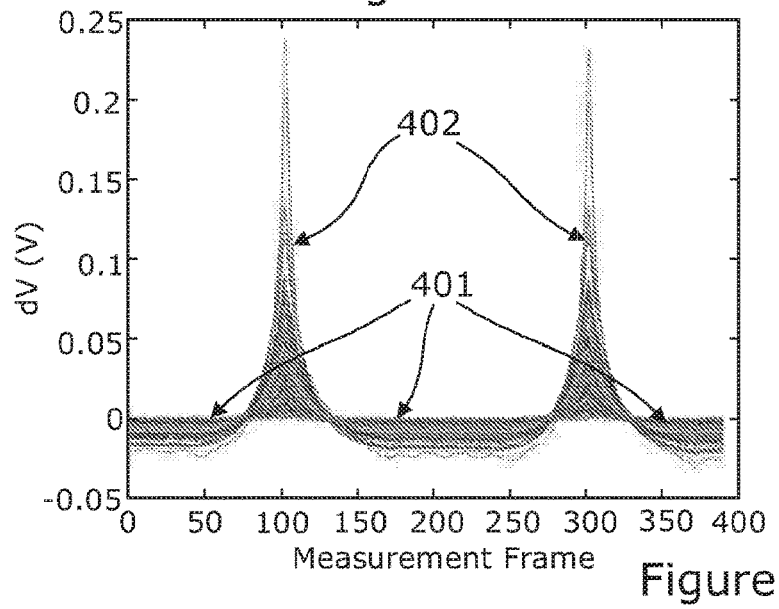
Figure 6
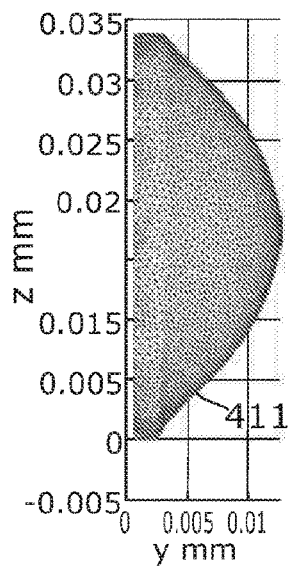 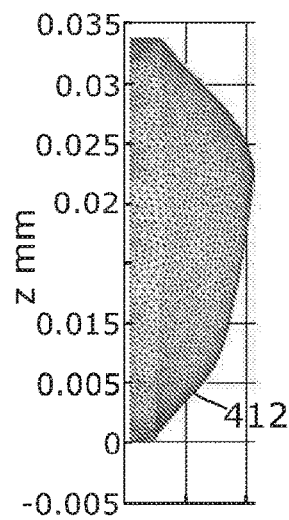 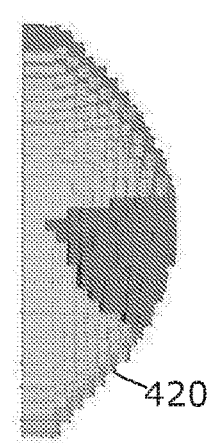
Figure 7　　　Figure 8　　　Figure 9

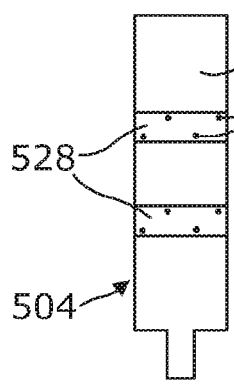 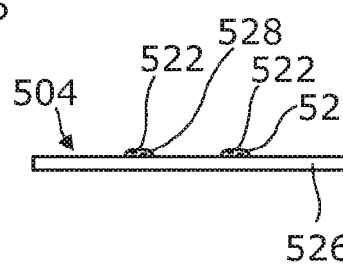 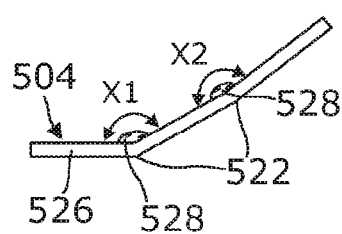
Figure 10a        Figure 10b        Figure 10c
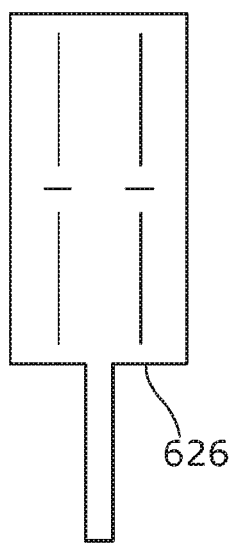 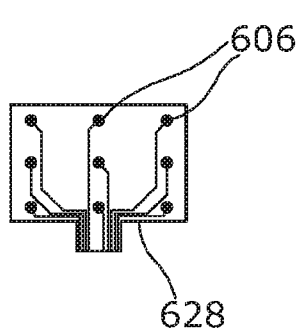 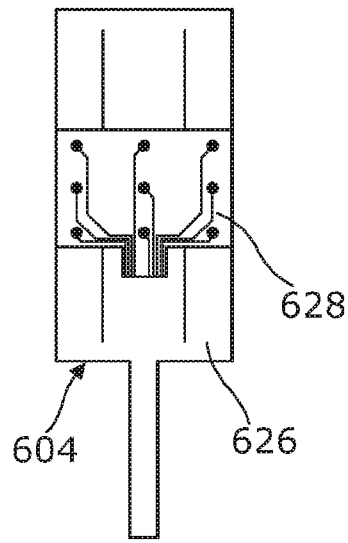
Figure 11
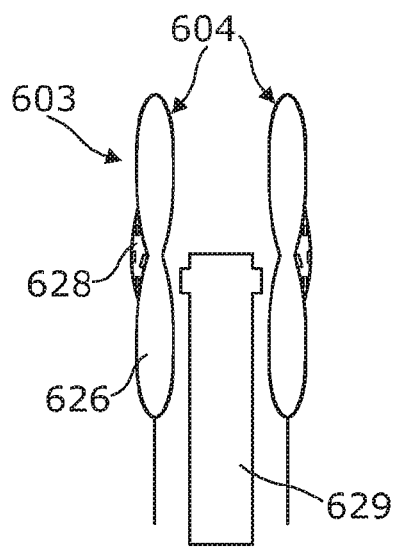 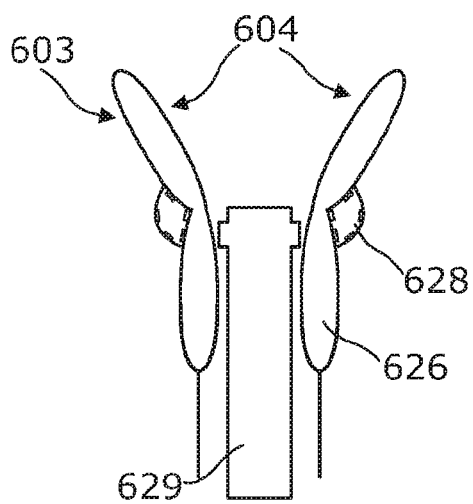
Figure 12a        Figure 12b

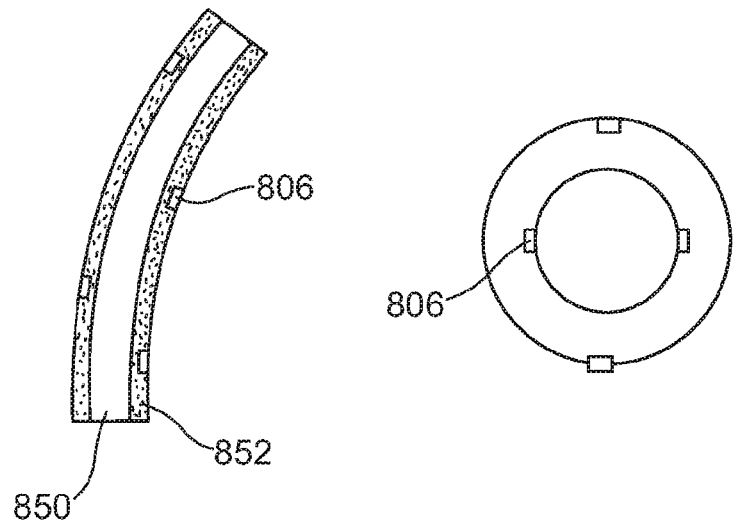
Figure 15a
Figure 15b
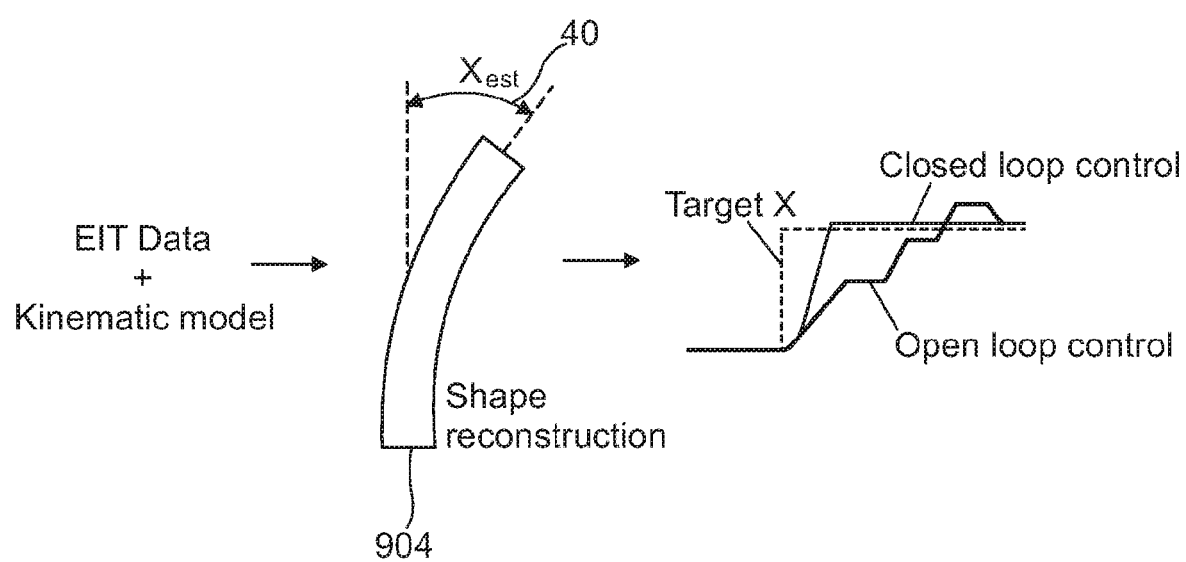
Figure 16a
Figure 16b

SENSOR SYSTEM FOR DETERMINING THE SHAPE OF A DEFORMABLE STRUCTURE

CROSS-REFERENCE TO RELATED APPLICATIONS

This application is a National Phase application under 35 U.S.C. 371 of PCT/GB2019/053657, filed Dec. 20, 2019, and claims the benefit of and priority to G.B. Application No. 1821129.2, filed Dec. 21, 2018, the disclosures of which are hereby incorporated herein by reference in their entirety.

This invention relates to a sensor, and particularly, but not exclusively, to a sensor for sensing the position and/or shape of a soft robotic device. The invention also relates to a method for determining the shape and/or position of a deformable structure, such as a soft robotic device.

Such a sensor has application in the field of minimally invasive surgery (MIS). MIS is being used with increasing frequency as an alternative to open surgery because of the improvements it can bring to patient safety and recovery time.

Surgical applications that benefit from MIS include reconstructive surgery, haemostasis, ischaemia detection, achalasia, gastric balloons/bands, catheters, balloons for heart bypass, auto-bionics. These, and other, applications may thus benefit from soft robots enhanced with sensors of this type.

Since the advent of laparoscopy, surgical technology has advanced on an exponential scale that has broadened the accessibility of the surgeon to the operative field with minimal incisions. MIS is usually carried out through natural body openings or small artificial incisions, usually resulting in reduced patient trauma, shortened hospitalisation, improved diagnostic accuracy and therapeutic outcome.

However, currently, the instruments used in MIS are rigid and, in the case of endoscopes or laparoscopic instruments, are difficult to control due to their long relative length and ergonomically unnatural controls. As the tools are also rigid, their use results in risk of unintentional damage to soft tissue which negates from the theoretical advantages of MIS techniques.

In the field of soft robotics, compliant materials are used to construct robotic devices that deform easily, making them highly applicable to interactions with soft tissue in MIS.

The next generation of surgical robotic devices will be designed to achieve access to all parts of the body from remote entry points, meaning they must be flexible and capable of navigating highly complex paths—all without causing damage to soft tissues.

A problem with soft robotic devices is that they are difficult to model, as both the structures of soft robots and the methods by which they achieve locomotion or actuation of joints rely on deformable materials. These materials exhibit non-linear responses to strain, so predicting the shape of soft devices and controlling the end effector is challenging, especially when external forces are exerted on the device.

Control would be facilitated if the bending angles of a soft device could be accurately measured. However, current shape sensing methods have limitations in terms of accuracy, robustness, compactness and deformability.

It is known to use electromagnetic (EM) tracking to track single points in space. However, a problem with this known technique is that the measurements are influenced by stray EM fields from other equipment. This makes shape reconstruction impossible and makes it difficult to integrate into an operating theatre with other electrical equipment.

In addition, it is known that imaging techniques such as fluoroscopy require large doses of radiation or contrast agents and either a C-arm or a monoplane X-ray system, while others such as ultrasound have low resolution and impair the flow of a surgical procedure.

It is also known to use optical tracking methods to track objects. However, such techniques require line of sight to the device and are therefore impractical or unsuitable in MIS applications.

Soft strain gauges made of Eutectic Gallium Indium (EGaIn) have been used to sense contact, strain and shear deformation of the surface to which they are affixed. However, EGaIn is expensive and lacks the biocompatibility important to MIS applications. Furthermore elastomer strain gauges give just a single degree of freedom and are either complex and costly to manufacture or too bulky to use in the restricted spaces imposed by MIS.

Fibre Bragg gratings (FBG) have been used to measure strain experienced by soft robotic devices. However, the location of a localized deflection cannot be determined, and the measurements are not sensitive in all directions. Therefore, a large number of sensor elements would be needed along the length of a device to fully sense the shape.

Electrical Impedance Tomography (EIT) is a sensing technique that infers variations in electrical impedance of electrically conductive media within a certain domain from voltage measurements made by electrodes positioned at the boundary of that domain.

Typical EIT techniques involve the placement of multiple electrodes positioned around the boundary of a domain such as a human chest or a chemical reaction chamber. An electric current is then injected between a pair of the electrodes and the resultant voltages that pass throughout the domain are measured by each of the remaining electrodes. This process is then repeated by sequentially injecting currents through different electrode pairs and eventually an image of the domain can be constructed based on the impedance inferred throughout the domain from the various measurements made by the distributed electrodes.

According to a first aspect of the invention there is provided a sensor system comprising:
- a deformable structure;
- a plurality of electrodes operably connectable to the deformable structure;
- an electrical conductor operably connected to the deformable structure and electrically couplable to each of the electrodes;
- a current source connectable to predetermined electrodes;
- a current injector for injecting current from the current source through predetermined electrodes;
- a voltage recorder for recording the voltage between predetermined pairs of electrodes; and
- an analyser for analysing voltage recordings to thereby determine the shape of the deformable structure.

The present invention provides a sensor system comprising a deformable structure. The deformable structure may be in the form of an actuator of the type known as a soft robot.

In the field of robotics, the term 'soft' refers to highly compliant materials that adapt to their surroundings in a similar way to those found in living organisms. Soft robotics is a subfield of robotics in which soft materials are used to construct robots, allowing for increased flexibility and adaptability in contrast to the rigidity commonly associated with standard robots. An important element of soft robotics is biomimicry, whereby the developers of soft robots are looking to the materials and actuation mechanisms present in nature for inspiration. One example is the way that plant cells utilise hydrostatic pressure to change the shape of leaves or petals in response to changes in the environment.

The system comprises an electrical conductor which is operatively connected both to the deformable structure and to a plurality of electrodes. The electrodes are each also operably connectable to the deformable structure.

A current may be injected through predetermined electrodes, and the voltage recorder is adapted to record the voltage generated between predetermined pairs of electrodes and caused by the injection of the current through the predetermined pair of electrodes. An analyser is then used to analyse the impedance recordings in order to determine the shape and position of the deformable structure.

The voltage recordings are analysed using electrical impedance tomography (EIT) techniques.

By means of the present invention, a soft robotic actuator may become proprioceptive (self-sensing) as well as being aware of its position relative to its surroundings.

In embodiments of the invention, the current injector is adapted to inject current from the current source through a predetermined sequence of electrodes. In some embodiments of the invention the current injector is adapted to inject current from the current source through a predetermined sequence of pairs of electrodes.

In embodiments of the invention, the current source is a source of constant current. In such embodiments of the invention an impedance dependent signal is created through the injection of the constant current.

In some embodiments of the invention, the current source is connectable to some, but not all, of the electrodes. However, in other embodiments of the invention, the current source is connectable to each of the electrodes. In such an embodiment, it is possible to inject a current through a plurality of predetermined pairs of electrodes at the same time.

Similarly, in embodiments of the invention, the voltage recorder may be connectable to each of the electrodes. In such embodiments of the invention it is possible to record the impedance between a plurality of predetermined pairs of electrodes at the same time.

In embodiments of the invention, the current source is connectable to a predetermined pair of electrodes, and the voltage recorder is connectable to each of the remaining electrodes.

In other embodiments of the voltage recorder is connectable to the predetermined pair of electrodes.

In embodiments of the invention, there may be a plurality of current sources, each of which current sources is connectable to predetermined electrodes. In such embodiments, a current may be injected simultaneously to more than one pair of electrodes.

In embodiments of the invention, the or each current source is a source of alternating current.

In some embodiments of the invention, each current source produces an alternating current having a frequency that is different to the frequency of alternating current produced by other current sources. In some embodiments of the invention, each current source may operate at a different frequency to each other current source. In other embodiments of the invention, more than one current source may operate at the same frequency.

In such embodiments of the invention, frequency division multiplexing may be used to enable more than one measurement to be taken and recorded at the same time. This means that more data may be obtained in real time. Such embodiments of the invention are particularly useful when used to determine the shape and position of a soft robotic device used in minimal invasive surgery, since it is possible to obtain real time, or near real time information about the position and shape of the soft robotic device.

Typical EIT systems inject current between sequential pairs of electrodes, known as Time Division Multiplexing (TDM).

However, the need within TDM EIT to switch between electrode pairs imposes a limit on the data acquisition rate.

By injecting multiple frequencies simultaneously through different electrode pairs Frequency Division Multiplexing (FDM) removes the need to switch entirely, making it a more suitable technique for real-time shape sensing. This is achieved by having a number of current sources working in parallel, each to inject an alternating current with a predetermined frequency through different electrode pairs. By recording multiple sets of impedance data simultaneously, an accurate reconstruction of the electrical conductor's shape can be formed instantaneously and then updated in real time or near real time.

The EIT method, and particularly the FDM EIT method, provides more information than the tracking of a small number of single points and does not require line of sight or a controlled environment, as in electromagnetic tracking and optical tracking. As such, this method is highly suitable to unstructured environments with limited space.

In embodiments of the invention, the electrodes are electrically isolated from the surrounding environment.

In such embodiments, the electrodes can be electrically coupled to the electrical conductor in a manner that isolates the measurements from the surrounding environment, therefore, results can be obtained reliably. Furthermore, as the electrical signal is confined within the device, it is non-invasive and biocompatible.

In embodiments of the invention, the deformable structure is an inflatable structure.

In such embodiments of the invention, the electrical conductor may comprise an electrically conductive fluid forming part of the deformable structure. In particular, the electrically conductive fluid may fill the deformable structure. In such embodiments of the invention, the deformable structure may be pressurised or otherwise inflated and/or depressurised or otherwise deflated by controlling flow of the electrically conductive fluid into and out of the deformable structural.

A particular advantage of such embodiments of the invention is that the deformable structure may be positioned in situ in a deflated condition. Once the deformable structure has been positioned appropriately, the electrically conductive fluid may be pumped or may otherwise enter the deformable structure in order to pressurise or otherwise inflate the structure.

In embodiments of the invention the sensor system further comprises a palpation sensor and the deformable structure forms part of the palpation sensor.

In such embodiments of the invention the plurality of electrodes and the electrical conductor may each also form part of the palpation sensor.

Palpation is a medical technique for diagnosis in which a practitioner would feel an area of a patient's body with his/her fingers or hands during a physical examination. The method therefore relies on touch rather than any other sense, such as sight or chemical sensing.

A palpation sensor (sometimes referred to as a tactile sensor or tactile palpation sensor) is a sensor that allows a practitioner to perform palpation techniques without using his/her fingers or hands, instead the sensor is able to 'feel' the area in question. Such a sensor may be particularly advantageous for use in MIS applications where a surgeon would typically feel an area of internal body tissue with his/her fingers or hands during an equivalent standard surgical procedure.

In such embodiments of the invention the deformable structure may be inflated with an electrically conductive fluid. In use, the deformable structure may be positioned against an area of internal tissue such that the deformable structure conforms to the surface it is positioned against. The change in shape of the deformable structure may be measured in correlation to a corresponding change of voltages recorded by the plurality of electrodes. Therefore the palpation sensor is able to 'feel' the shape of the internal tissue based on the deformation which is experienced by the deformable structure.

In embodiments of the invention, the electrically conductive fluid comprises a saline solution.

In some embodiments of the invention, the electrical conductor comprises an outer layer of the deformable structure.

In such embodiments of the invention, the electrical conductor may be in the form of a skin enclosing some or all of the deformable structure.

An advantage of such embodiments of the invention, is that the electrical conductor may be attached to an existing deformable structure.

In such embodiments of the invention the electrical conductor may comprise a fabric or material made from a conductive material.

In some embodiments of the invention, the electrical conductor may also serve as an actuation mechanism for producing movement in the actuator.

For example, in embodiments of the invention in which the electrical conductor comprises an electrically conductive liquid, the liquid may also serve as a means for producing movement in the actuator. For example, by changing the pressure of the liquid within the actuator, movement such as bending may result. In such embodiments of the invention, the conductive liquid acts as both the electrical conductor and a fluidic actuator. The movement that may be produced in such embodiments of the invention may include bending motion and variable stiffness.

In embodiments of the invention the sensor system further comprises a retraction device and the deformable structure forms part of the retraction device.

In such embodiments of the invention the plurality of electrodes and electrical conductor may each also form part of the retraction device.

In the field medicine, and particularly surgical medicine, a retraction device is a device for the retraction of a region of tissue to expose underlying tissue beneath it, thereby providing the surgeon with better visibility of the underlying area.

The electrical conductor of a retraction device according to an embodiment of the invention may serve as an actuator wherein actuation of the deformable structure causes a bending movement which may be used to retract internal body tissue.

In embodiments of the invention the sensor system further comprises a flexible printed circuit (FPC) wherein each of the plurality of electrodes is coupled to the FPC.

In such embodiments of the invention, the FPC may comprise a flexible connection element which provides an electrical connection to the plurality electrodes.

A sensor according to such embodiments of the invention may readily be manufactured according to the following method:

The FPC may be adhered to a first part of an outer skin such that a chamber is formed between the FPC and the outer skin, and the flexible connection element extends from the chamber.

A laser welding process may then be used to seal the chamber by welding a second part of the outer skin to the first part in a given pattern such that the outer skin encases the FPC.

The flexible connection element may be left unsealed at this stage before adhesive is used to make the outer skin watertight around the flexible connection element.

The flexible connection element provides a rapid connection to the plurality of electrodes that are now located in the interior of the inflatable chamber.

According to a second aspect of the present invention there is provided a method for determining the shape of a deformable structure comprising the following steps:
  arranging a plurality of electrodes on or in the deformable structure such that each electrode is adapted to be operably connectable to the deformable structure;
  placing an electrical conductor such that it is operably connected to the deformable structure and is electrically couplable to each of the electrodes;
  injecting a current from a current source through predetermined electrodes,
  recording the voltage between predetermined pairs of electrodes, and
  analysing the voltage recordings to determine the shape of the deformable structure.

By means of the present invention it is possible to determine the shape of a soft robot via the recording of impedance between predetermined electrodes.

In embodiments of the invention, the step of injecting a current from a current source through predetermined electrodes comprises the step of injecting a current from the current source sequentially through a plurality of predetermined electrode pairs, and the step of recording the voltage comprises recording voltage during each current injection to thereby record a plurality of voltages, wherein each voltage is recorded between a predetermined electrode pair, and the step of analysing comprises the step of analysing the plurality of voltage recordings in combination to determine the shape of the deformable structure.

In embodiments of the invention, the step of injecting a current comprises injecting a current with a predetermined current frequency from each of a plurality of current sources through a predetermined electrode pair selected from the plurality of electrodes, the step of recording voltage comprises recording a plurality of voltages wherein each voltage is recorded between a predetermined pair of electrodes.

In embodiments of the invention comprises the further steps of:
  controlling the movement of a soft robot comprising the steps of:
  (a) setting a goal position for the deformable structure to achieve by controlling movement of the soft robot;
  (b) evaluating the shape of the deformable structure;
  (c) initiating movement of the soft robot towards reaching that goal;
  (d) re-evaluating the shape of the deformable structure;
  (e) repeating steps b-d until the goal set in step a is achieved.

Measuring or inferring the shape/deflection of the robot means it can be used in a feedback loop as a process variable. This enables closed loop control, allowing for correction of any deviation in expected signal.

Open loop control is control in absence of feedback, which is of limited use in soft robotics in MIS applications, as the environment is likely to change, and thus deviations from expected behaviour are likely.

The invention will now be further described by way of example only with reference to the accompanying figures in which:

FIG. 1 is a schematic representation of a sensor according to a first embodiment of the invention;

FIG. 2*a* is a schematic representation of a double hinged actuator forming part of the sensor according to an embodiment of the invention;

FIGS. 2*b* and 2*c* are schematic representations of the double hinged actuator of FIG. 2*a* expanding and actuating respectively, in response to pressurisation.

FIGS. 3*a* to 3*d* are schematic representations illustrating how the actuator of FIGS. 3*a* to 3*c* is constructed;

FIG. 4*a* is a schematic representation showing the positioning of electrodes in the actuator of FIGS. 2*a* to 2*c*;

FIG. 4*b* is a schematic representation showing the current injection electrode pairs of the actuator of FIGS. 2*a* to 2*c*;

FIG. 4*c* is a graph representing how the impedance signal recorded between the current injection electrode pairs of FIG. 4*b* varies according to the shape of the actuator;

FIG. 5 is a schematic representation of a palpation sensor forming part of a sensor according to an embodiment of the invention;

FIG. 6 is a graph showing changes in EIT voltages recorded over time in the palpation sensor shown in FIG. 5;

FIG. 7 is a graphical model of the palpation sensor shown in FIG. 5 when filled with an electrically conductive fluid;

FIG. 8 is a graphical model of the palpation sensor shown in FIG. 5 when deformed by its environment;

FIG. 9 is a schematic reconstruction of the palpation sensor shown in FIG. 5 which highlights the localised deformation shown in FIG. 8;

Figures 2A, 2B, 2C:
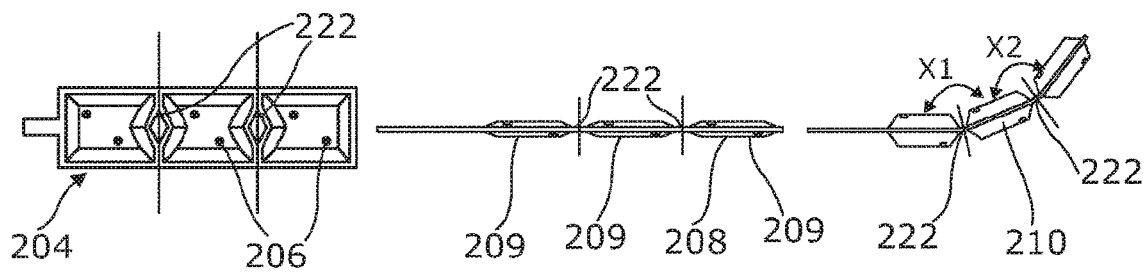
Figure 13:
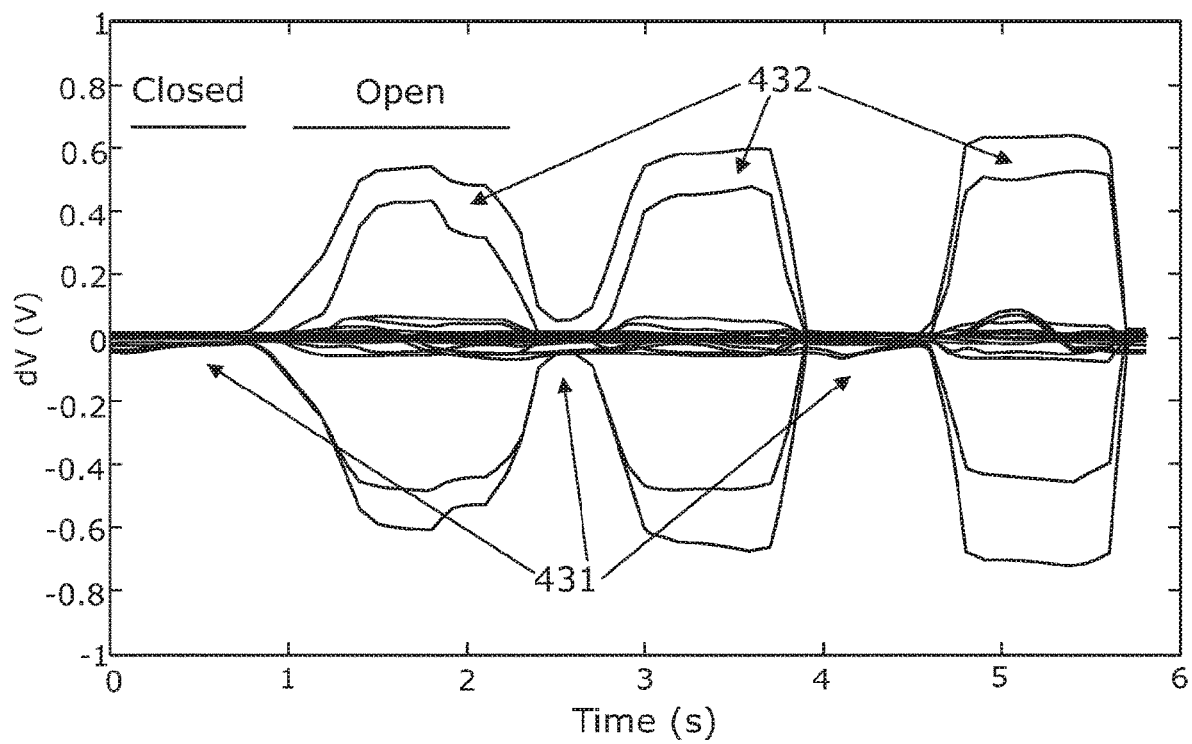
Figures 14A, 14B, 14C, 14D:
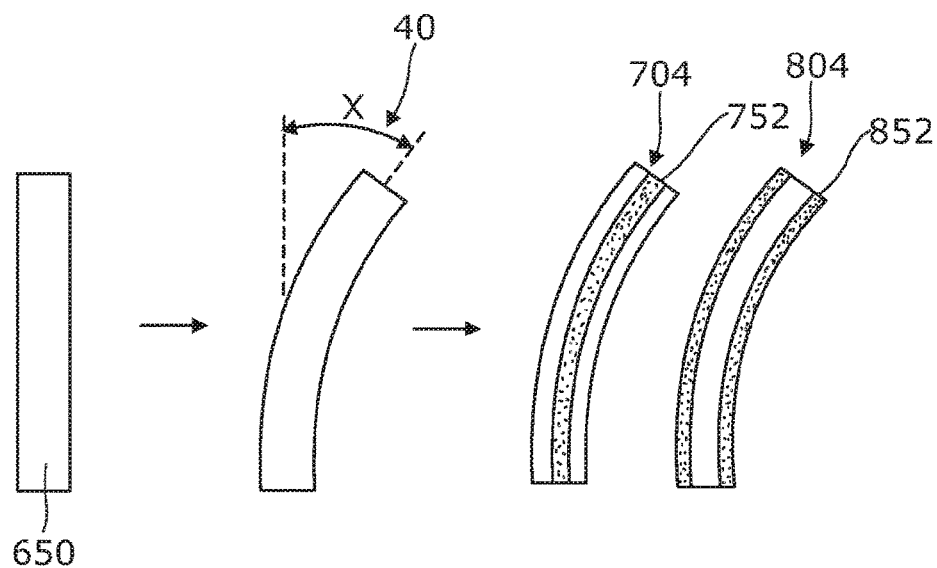
Figure 17:
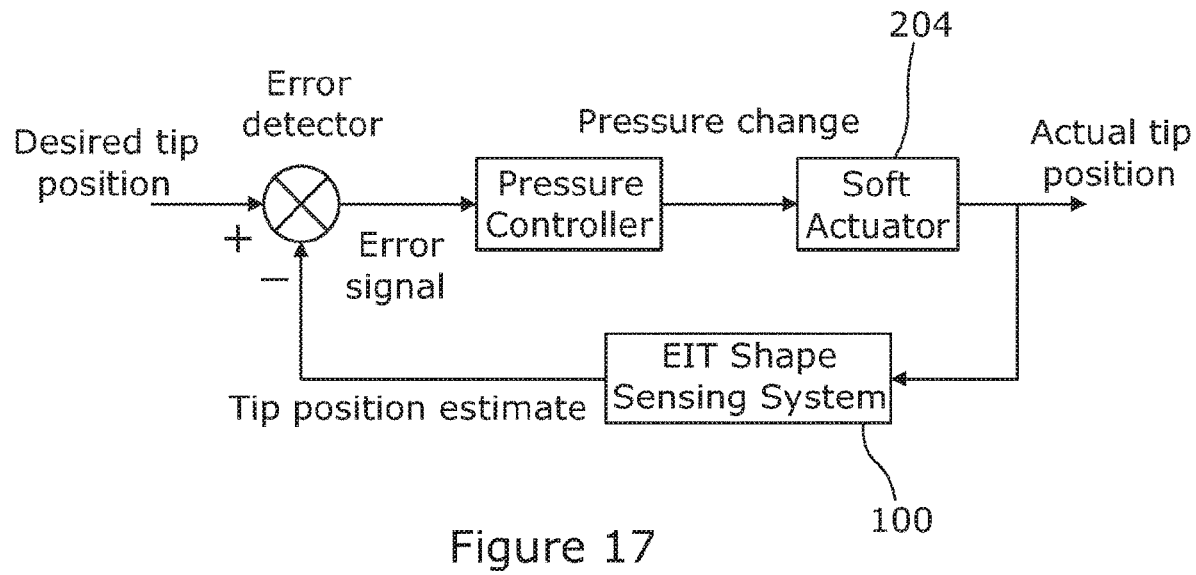

FIG. 10*a* is a schematic representation of a double hinged pneumatic finger forming an actuator forming part of a sensor according to another embodiment of the invention;

FIGS. 10*b* and 10*c* are schematic representations of the double hinged pneumatic finger of FIG. 10*a* shown expanding in response to pressurisation;

FIG. 11 is a schematic representation of a single hinged pneumatic finger forming part of an actuator forming part of a sensor according to an embodiment of the invention;

FIGS. 12*a* and 12*b* are schematic representations of actuator forming part of a sensor according to an embodiment of the invention;

FIG. 13 a graph showing changes in EIT voltages recorded over time in the actuator shown in FIGS. 12*a* and 12*b*;

FIGS. 14*a* and 14*b* are schematic representations of an actuator according to another embodiment of the invention formed from a deformable structure;

FIGS. 14*c* and 14*d* are schematic representations showing how the actuator of FIGS. 14*a* and 14*b* may be adapted to form a sensor according to an embodiment of the invention;

FIGS. 15*a* and 15*b* are schematic illustrations showing the position of electrodes forming part of the sensor shown in FIG. 14*d*;

FIG. 16*a* is a schematic representation of a target actuator shape;

FIG. 16*b* is a graphical representation of closed and open loop control schemes to achieve the target actuator shape shown in FIG. 16*a*;

FIG. 17 is a schematic representation of a closed loop control system used to control the soft actuator of FIG. 2*a*

Figure 18:
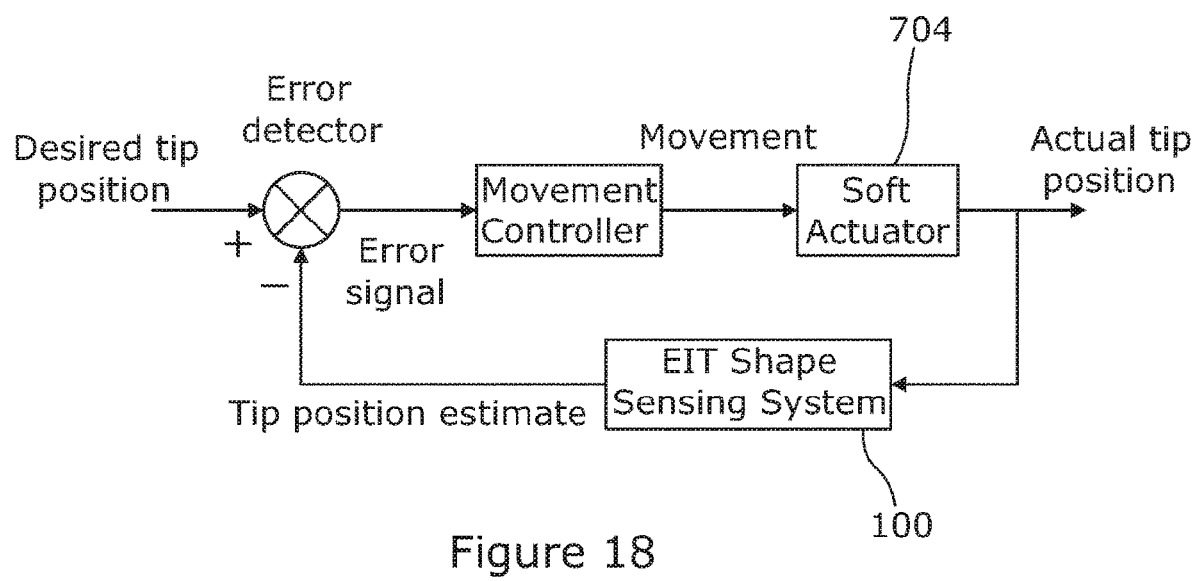

FIG. 18 is a schematic representation of a closed loop control system used to control the soft actuator of FIG. 14*c*.

Figure 1:
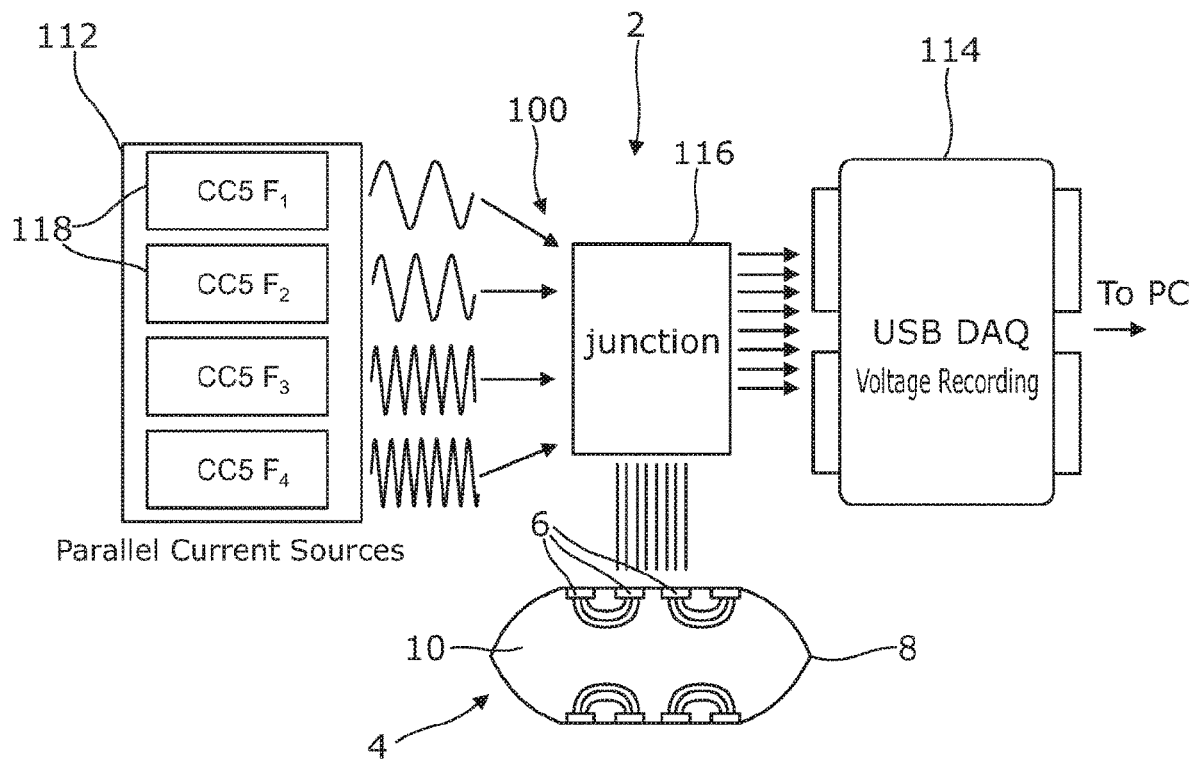

Referring initially to FIG. 1 a sensor according to an embodiment of the invention is designated generally by the reference numeral 2. The sensor 2 comprises an actuator in the form of deformable structure 4. Embedded into the surface of the actuator 4 is a plurality of electrodes 6. In this embodiment of the invention the actuator 4 comprises an inflatable structure comprising an outer skin 8 which is in the form of an electrical insulator. The actuator 4 comprises an electrical conductor which in this embodiment comprises a conducting fluid 10 which fills the actuator 4. The electrically conductive fluid 10 may be any suitable fluid, and in this example comprises a saline solution.

The electrodes are connected by conductive tracks and the electrodes and the tracks are formed in a conductive layer embedded in the outer skin of the actuator 4. The outer skin is shaped such that the electrodes and connector pads only are exposed.

This may be achieved by using any convenient process such as by using sputtering techniques, transfer or inkjet printer for example.

The sensor 2 comprises an EIT system 100. The EIT system comprises an alternating current source 112, a voltage recorder 114 and the plurality of electrodes 6. The EIT system 100 further comprises a means for addressing specific electrodes 6 in order to inject current between predetermined pairs of electrodes. In the illustrated embodiments, the means for addressing specific electrodes comprises a junction 116. The junction may be any suitable junction and may for example comprise a switch network which may be implemented by daisy-chained switch ICs or multiplexer ICs. This embodiment may be implemented using a manual plug board using jumper wires although this would be at the expense of configurability. The electrodes 10 are connected to the current source 112 and to the voltage recorder 114 by means of the junction 116.

In the illustrated embodiment the alternating current source 112 comprises four parallel current sources 118 each providing an alternating current having a frequency that is different to the frequency provided by all other current sources.

By means of the parallel current sources 118, a plurality (here 4) of frequencies may be injected simultaneously through different pairs of electrodes 10. This is achieved using frequency division multiplexing (FDM) which removes the need to switch. This makes the invention particularly suitable for shape sensing.

Although the illustrated embodiment comprises four parallel current sources, in other embodiments there may be more or fewer current sources, and in some embodiments of the invention there are six independent current sources 118. In such an embodiment each source can inject current at 165 µA between 10 Hz to 100 kHz between a single pair of electrodes, well below the IEC 60601 safety limits.

The voltage recorder 114 comprises a National Instruments (NI), USB-6216 16-bit DAQ at a 50 kHz sampling rate.

The current sources 118 and the voltage recorder 114 are connected to the electrodes 10 using a custom PCB.

To obtain a single EIT measurement, the voltage recorded on a single electrode is demodulated at a single frequency and averaged over several sign wave periods.

In embodiments of the invention, the range of 3 ms to 250 ms was selected to take into account the limitations of USB data transfer speeds and DAQ buffer size.

The system also comprises an analyser 120 which may be in the form of a personal computer (PC) for example.

Each current source 118 is used to apply an alternating current across a predetermined pair of electrodes 10. The junction 116 allows the electrodes 10 to be individually addressed so that an alternating current may be applied across any two electrodes as necessary. The voltage recorder records the impedance across pairs of electrodes and the impedance information is analysed via an analyser such as a PC.

The sensor may be used with a wide range of deformable actuators.

Referring now to FIGS. 2a to 2c, a sensor according to another embodiment of the invention is illustrated. The illustrated sensor comprises a deformable hinged actuator 204 which, in this embodiment is a fluid actuated hinge adapted to bend at an angle predefined by the aspect ratio of a diamond weld pattern formed in a central portion of the actuator 204. The actuator 204 further comprises a plurality of electrodes 206.

In the specific embodiment described, the actuator 204 comprises a chain of two hinges 222 connected in series to produce a curling actuator having a chamber 209 segmented into three regions by the hinges 222, as shown in FIG. 2c.

Referring now to FIGS. 3a to 3d details of a method of forming the actuator 204 is illustrated.

Initially, the number and positioning of electrodes 206, as well as the selection of EIT measurement protocol (the choice of current injection and measurement electrodes) requires optimisation for each application.

In the illustrated embodiment of the invention, a Finite Element Model (FEM) is created replicating the geometry of the deformable structure with candidate electrode positions. A sensitivity analysis is made using EIT forward modelling software, which estimates the change in voltages during expected changes in shape. This information is then used to identify regions of low sensitivity or redundancy in the measurements, which is then used as feedback to update the electrode positions and measurement protocol for the next modelling iteration.

The forward problem in EIT is a combination of the quasi-static Maxwell equations with the addition of the Complete Electrode Model boundary conditions for a single pair of electrodes (l=1,2)

$$\nabla \cdot \sigma \nabla u = 0, \quad (1)$$

$$\sigma \frac{\delta u}{\delta n} = 0 \text{ off } \bigcup_{l=1}^{2} e_l \quad (2)$$

$$u + z_l \sigma \frac{\delta u}{\delta n} = V_l, l = 1, 2 \quad (3)$$

Where $\sigma$ is the conductivity, u is the electric potential, n is the normal to the boundary, $e_l$ is the lth electrode boundary, $z_l$ is the contact impedance on the lth electrode, and $V_l$ are the measured voltages. The finite element method is then employed to solve a discretized form of (1) for a specific domain. This is then repeated for all injection pairs and measurement electrodes. Typically, a linear relationship between voltage changes and conductivity changes is made, allowing for a construction of a Jacobian matrix J, which maps the changes in conductivity in each element to changes in voltage all electrodes:

$$\delta u = J \delta \sigma \quad (4)$$

However, as the aim is to reconstruct conductivity changes from voltages measurements (2) must be inverted. However, as J is ill-conditioned, regularization is necessary before it can be inverted.

Regularisation is then employed to limit the output to a realistic conductivity distribution. These reconstructions are performed on a coarser subdomain than the tetrahedral FEM in the forward problem.

Example regularisation schemes are Zeroth order Tikhonov, First Order Tikhonov, Total Variation and NOSER. The regularisation hyperparameter is chosen through objective means, such as cross-validation or L-curve:

$$\widehat{\delta \sigma} = \arg \min_{\delta \sigma} \|\delta v - J \delta \sigma\|^2 + \lambda \|\delta \sigma\|^2 \quad (5)$$

$$J_\lambda^{-1} = (J^T J + \lambda I)^{-1} J^T \quad (6)$$

Where $\widehat{\delta \sigma}$ an estimated conductivity change, $\delta v$ are the boundary voltage change and $\lambda$ is a hyperparameter controlling the extent of the regularization. The reconstructions were performed using the method developed by Aristovich et al., [K. Y. Aristovich, G. S. dos Santos, B. C. Packham, and D. S. Holder, "A method for reconstructing tomographic images of evoked neural activity with electrical impedance tomography spp. 1095-109, June 2014.] with $\lambda$ selected through cross-validation in a hexahedral subdomain.

Solid model approximations of the deformable structure are designed and used to create tetrahedral FEMs.

Once the location and positioning of the electrodes has been optimised, the layout of the electrode traces can be designed. This step involves two layers. The first layer is a highly conductive layer which is equivalent to the copper in traditional printed circuit boards and which forms the electrodes and tracks. The second layer is the insulation layer which ensures the electrodes and connector pads only are exposed. This could be achieved by a number of processes such as sputtering, transfer or inkjet printing.

In the case of the inflatable deformable structure 204 of the type shown in FIGS. 3a to 3c, the electrodes 206 are deposited onto sheets 224 which may be made from plastics materials. The electrodes are aligned with a weld pattern before being laser welded to form the outer skin 208 of the actuator 204.

As shown in FIGS. 3a to 3d, a chain of two hinges 222 is connected in series to produce an actuator 204. In this embodiment, the double hinge actuator 204 has a length of approximately 200 mm and a width of approximately 500 mm and a very low profile. The two diamond shaped hinges 222 measure approximately 20 mm by 10 mm. The hinges 222 are shown schematically in FIGS. 2c and 2d.

FIG. 3c also shows the application of an IR absorbing dye which is deposited by for example a robotic arm using an adapted pen to mark out where the two sheets 224 should be welded together.

The finished product is then shown in FIG. 3d after the two sheets 224 have been welded together. Any excess sheet material may be simply cut from around the welded device and fluid inlet tubes may be connected to the device. It is possible to incorporate features having sizes down to 1 mm due to the techniques used to create and weld the device together.

A plurality of hinges may be welded into a single chamber, a plurality of chambers may be welded in a single layer and also a plurality of layers may be stacked and welded together after an alignment step. A variety of designs for fluidic actuators with integrated EIT sensors according to embodiments of the invention may be produced using the described method, thereby enabling a very wide range of applications to benefit from embodiments of the invention.

The actuator 204 may then be placed in situ before being pressurised or otherwise inflated with a conductive liquid 210 which in this case is a saline solution.

Referring now to FIG. 4a a side view of the double hinged actuator 204 is shown in more detail. The actuator 204 is shown in side profile has six electrodes 231, 232, 233, 234, 235 and 236 as shown in the figure and one chamber 209.

Given the symmetry of the design, there are three possible injection pairs.

For example, current may be injected at 2, 4 and 6 kHz between the pairs of electrodes shown in FIG. 4b. Voltages may then be recorded between each pair of electrodes opposite to the injection pairs. In other words, recording between 234-235, 232-233 and 231-236 for injection between each of the pairs shown in FIG. 4b. This means a total of nine measurements may be taken.

In this embodiment of the invention, the regions of chamber 209 in the actuator 204 are independent.

The voltage measurements taken while current is being injected into the top two current injection pairs in FIG. 4b are largely independent because of the concentration of current localised around the electrodes injecting current. When injecting between electrodes 233 and 236, negligible current flows into the first chamber region 209a, so this measurement is not sensitive to changes of shape of that chamber, or in the first hinge 222a. It is sensitive only to where the current flows, which is between the second 209b and third 209c chamber regions, and due to the design, it is most sensitive to the shape change in the second hinge 222b.

This means that a single multiple-channel impedance measurement that is sensitive only to the change of shape of the hinge of interest is possible for both the first hinge 222a and second hinge 222b respectively, as shown in FIG. 4c. In FIG. 4c, the channels 2, 4 and 5 show change in impedance, and therefore shape, of the conductor at first hinge 222a, while the channels 3, 7 and 9 in FIG. 4c show change in impedance, and therefore shape, of the conductor at second hinge 222b. Channel 1 in FIG. 4c shows a change in impedance of the conductor on the interior of the soft actuator due to changes in either the first hinge 222a or the second hinge 222b.

In this embodiment, the wires connecting the electrodes to the current source and voltage recorder may be in close proximity. This might cause capacitive coupling leading to interference between signals on different wires. The separation of the two injection frequencies may be increased to 10 kHz to minimise capacitive couplings. Capacitive coupling or crosstalk can mean that signals on one wire cause interference on nearby ones. By making the spacing between frequencies higher, it makes it easier to filter out any interferences which might occur. This was done in the case of the finger actuator 504 illustrated, because the wires used in the prototype had to be in close proximity.

Referring now to FIG. 4c, changes during manual rotation of each axis in turn of the actuator shown in FIGS. 4a and 4b is illustrated.

It can be seen that there are large changes in the corresponding channels when the first hinge 222a is moved, but smaller changes when the second hinge 222b is rotated. However, for the injection across the whole sensor, changes are seen in every case.

Referring now to FIG. 5, a palpation sensor 304 forms part of a sensor system according to an embodiment of the first aspect of the invention. The palpation sensor 304 comprises an outer skin 308 and a flexible printed circuit (FPC) 340 which, in turn, comprises a plurality of electrodes 306 and a flexible connection element 341 providing an electrical connection to the plurality electrodes 306.

In this embodiment of the invention, the FPC 340 is adhered to a first part of the outer skin 308 such that a chamber 309 is formed between them. A laser welding process is then used to seal the chamber 309 by welding a second part of the outer skin 308 to the first part in a given pattern such that the FPC 340 is encased in the outer skin 308. The flexible connection element 341 is left unsealed at this stage before adhesive is used to make the outer skin 308 watertight around the flexible connection element 341. The flexible connection element 341, which extends from the chamber 309, provides a rapid connection to the plurality of electrodes 306 that are now located in the interior of the inflatable chamber 309. In this embodiment, there are sixteen electrodes 306 present, but there may be more or fewer electrodes present in other embodiments.

The chamber 309 may be inflated with an electrically conductive fluid (such as saline). In this embodiment of the invention, the FPC 340 further comprises an electroless nickel immersion gold (ENIG) surface finish which provides a sufficiently low impedance contact with the electrically conductive fluid (e.g. saline).

In use, the palpation sensor 304 may be used as a tactile palpation sensor which can be deployed endoscopically. Once inside the body, the chamber 309 may be inflated with electrically conductive fluid (e.g. saline) such that the palpation sensor 304 forms an inflated shape 411 shown in FIG. 7. The palpation sensor 304 may then be pressed against a tissue of interest, which deforms the surface of the sensor such that the palpation sensor 304 forms a deformed shape 412, an example of which is shown in FIG. 8 (although the deformation could cause any deformed shape). The change in shape results in changes in EIT voltages recorded by the plurality of electrodes 306. For example, the graph of EIT voltages shown in FIG. 6 comprises stable periods 401 that indicate no deformation to the sensor and peaks 402 which indicate a deformation is taking place. The changes in voltages can then be reconstructed into an EIT image 420, showing the region of the sensor that was deformed, an example of which is shown in FIG. 9. This is an improvement over existing pressure sensors used for palpation as it is not possible to localise the deformation on the pad surface of known palpation devices.

Turning now to FIGS. 10a to 10c, a deformable actuator 504 according to another embodiment of the invention is shown. In this embodiment the actuator comprises a finger actuator 504 comprising a pneumatic finger. The finger actuator 504 as shown in FIG. 10a comprises a pneumatic beam 526 and two hydraulically actuated chambers 528.

The pneumatic beam 526 comprises two actuated hinges 522 formed from the two hydraulically actuated chambers 528. By increasing the pressure in, or otherwise inflating, the chambers 528, the pneumatic beam 526 is caused to buckle as shown particularly in FIG. 10c.

The chambers 528 in the finger actuator 504 are each filled with an electrical conductor, in this case saline. Each chamber 528 is electrically isolated so current cannot be injected between the two chambers 528, nor can voltages be measured across electrodes 506 contained within separate chambers 528. Therefore, each chamber 528 can be treated independently. As each chamber 528 has only two electrodes 506 in this embodiment, there is only a single possible impedance measurement per chamber 528—injecting current and measuring between that single pair of electrodes 506. The deformation of each actuated hinge 522 can therefore be analysed independently. A greater or lesser number of chambers 528 incorporating a greater or lesser number of electrodes 506 can be added to a pneumatic beam 526 or other deformable structure to create controllable hinges 522.

Referring now to FIG. 11, a soft actuator 604 according to an embodiment of the invention is illustrated. The soft actuator comprises a pneumatic beam 626 and a hydraulically actuated chamber 628 coupled to the pneumatic beam 626. The chamber 628 comprises a plurality of electrodes 606 capable of EIT sensing.

Referring now to FIGS. 12a and 12b, a sensor system which may be used as a retraction device 603 comprises a pair of soft actuators 604 mounted to a flexible endoscope 629 such that the hydraulically actuated chambers 628 face away from the endoscope 629.

In FIG. 12a the chambers 628 are empty and the soft actuators 604 therefore have a low profile which allows the flexible endoscope 629 to move unencumbered.

In FIG. 12b the chambers 628 are inflated with a hydraulic actuation fluid, which also acts as an electrically conductive fluid, and the soft actuators 604 bend at the site at which they are coupled to the chambers 628. As the chambers 628 are positioned on the outward facing sides of the soft actuators 604, the soft actuators bend outwards, away from the flexible endoscope 629. The soft actuators 604 may be deployed in this way retract tissue away from a site on which a surgical procedure is to be performed, such as an endoscopy.

The plurality of electrodes may be electrically connected to an EIT system (such as that shown in FIG. 1) to provide a measure of the shape of the soft actuators 604 and, therefore, provide a measure of the degree of bending of each actuator 604. In this way, a desired bending angle can be set, and feedback may be provided by the EIT system of the current bending angle. The pressure of the hydraulic actuation fluid can then be modulated to alter the bending angle until the desired value is reached. Failure to reach the desired value within a safe pressure range may also give an indication that external forces are acting on the retractor, thus preventing the desired motion.

FIG. 13 shows a graph of EIT voltages recorded by a soft actuator 604 (similar to that shown in FIG. 6). The closed periods 431, with EIT voltages of approximately 0 dV, indicate that the chambers are empty. Whereas the open periods 432 comprise large peaks of voltage the values of which correlate to a bending angle. Hence an EIT system can be used to inflate/deflate the hydraulic actuation chambers in order to achieve a set bending angle as set out above.

Turning now to FIGS. 14a and 14d, a soft actuator 704 according to another embodiment of the invention is illustrated. The soft actuator 704 comprises an existing soft actuator 750 which is adapted to deform in the manner shown particularly in FIG. 14b, which shows the existing actuator 750 bending through an angle designated by the reference numeral 40.

The existing soft actuator 750 may be readily converted into an actuator suitable for use with a sensor according to embodiments of the invention by either introducing a conductive core 752 into the existing soft actuator 750 or by applying a conductive sheath 852 around the existing soft actuator 750 such that the conductive sheath surrounds the existing soft actuator 750.

Turning now to FIGS. 15a and 15b, an actuator 804 according to embodiments of the invention is illustrated schematically. The actuator 804 is shown to have an outer conductive sheath 852 with electrodes 806 embedded therein. The outer sheath 852 and electrodes 806 are shown more clearly in FIG. 15b.

For an external actuator as shown in FIGS. 15a and 15b, the electrodes 806 will be placed inside the mould used to create the conductive polymer, thus embedding the electrodes inside.

Turning now to FIGS. 16a and 16b, closed loop and open loop control is shown.

The deformation of an actuator can be understood with the aid of kinematic models which calculate estimates of the actuator's shape based on EIT data.

Therefore, EIT data recorded by the voltage recorder 114 is analysed against kinematic models by the analyser 120 to produce an estimated reconstruction of the actuator's shape or deflection 40 in real time or near real time as represented in FIG. 16a.

The reconstruction of the actuator is then used as a process variable in a control scheme. A target shape 40 (Target X), and thus target tip position, is set and in one embodiment a closed loop control scheme is used whereby the automated controller iteratively controls the actuator and then evaluates the estimated shape of the actuator before providing a further control input. In MIS applications, variations in the environment are likely to cause continuous and varied deformation to the shape of the actuator. The EIT sensors measure any deformation and the shape reconstruction changes accordingly. The automated controller can then react to these changes near to instantaneously and continue controlling the actuator towards the target shape. The closed loop scheme therefore enables the target to be reached efficiently and accurately, as graphically represented in FIG. 16b.

In a possible embodiment of the invention an open loop control scheme is used whereby the iterative feedback and control process is not performed autonomously but requires user input. The user is required to manually adjust the actuator in reaction to deformation caused by varying environments, this is represented by steps in the graph of FIG. 16b wherein the flat sections result from lag between the estimated shape reconstruction being displayed and the user then reacting and providing further input accordingly. This control scheme is less accurate and less efficient, particularly in applications such as MIS.

Turning now to FIGS. 17 and 18, examples of the closed loop control schemes discussed in relation to FIG. 16b are shown.

In one embodiment of the invention the closed loop control scheme shown in FIG. 17 is used to control the soft actuator 204. A desired tip position is inputted into the system, it is compared with a tip position estimated by the EIT shape sensing system 100 by the error detector. The difference between the desired and estimated tip positions is sent as an error signal to the pressure controller which varies the pressure in the chamber of the soft actuator 204 to alter the actual tip position. The EIT shape sensing system 100 creates a new estimate of the tip position which is sent to the error detector and the process is automatically repeated until there is no longer any error between the desired tip position and the estimated tip position.

In another embodiment the closed loop control scheme of FIG. 17 is used to control the soft actuator 504 in the same way as described for soft actuator 204. In a further embodiment the closed loop control scheme of FIG. 17 is used to control the soft actuator 604 in the same way as described for soft actuator 204.

In one embodiment of the invention the closed loop control scheme shown in FIG. 10 is used to control the soft actuator 704. Similarly, a desired tip position is inputted into the system, it is compared with a tip position estimated by the EIT shape sensing system 100 by the error detector. The difference between the desired and estimated tip positions is sent as an error signal to the movement controller which controls movement of the existing actuator 750 to alter the actual tip position. The EIT shape sensing system 100 creates a new estimate of the tip position which is sent to the error detector and the process is automatically repeated until there is no longer any error between the desired tip position and the estimated tip position.

In another embodiment the closed loop control scheme of FIG. 10 is used to control the soft actuator 804 in the same way as described for soft actuator 704.

The invention claimed is:

1. A sensor system comprising:
    a deformable structure;
    a plurality of electrodes operably connectable to the deformable structure;
    an electrical conductor operably connected to the deformable structure and electrically couplable to each of the electrodes;
    a plurality of current sources wherein each current source is connectable to predetermined electrodes and produces an alternating current frequency different to those produced by the remaining current sources;
    a current injector for injecting current from each current source through predetermined electrodes;
    a voltage recorder for recording the voltage between predetermined pairs of electrodes;
    an analyser for analysing voltage recordings to thereby determine the shape of the deformable structure; and
    a controller for controlling locomotion or actuation of a soft robot according to the determination of the shape of the deformable structure.

2. The sensor system according to claim 1, wherein each current injector is adapted to inject current from the current source through a predetermined sequence of electrodes.

3. The sensor system according to claim 1, wherein each current source is a source of constant current, and the voltage recorder is adapted to record an impedance dependent signal created through the injection of the constant current.

4. The sensor system according to claim 1, wherein the voltage recorder is connectable to each of the electrodes.

5. The sensor system according to claim 1 in which the electrodes are electrically isolated from the surrounding environment.

6. The sensor system according to claim 1, wherein the deformable structure is an inflatable structure.

7. The sensor system according to claim 6, wherein the electrical conductor is an electrically conductive fluid forming part of the deformable structure.

8. The sensor system according to claim 6, wherein the sensor system further comprises a palpation sensor and the deformable structure forms part of the palpation sensor and/or a retraction device and the deformable structure forms part of the retraction device.

9. The sensor system according to claim 1 wherein the electrical conductor comprises an outer layer of the deformable structure.

10. The sensor system according to claim 1, further comprising a flexible printed circuit (FPC) wherein each of the plurality of electrodes is coupled to the FPC.

11. A method comprising the following steps:
    arranging a plurality of electrodes on or in the deformable structure such that each electrode is adapted to be operably connectable to the deformable structure;
    placing an electrical conductor such that it is operably connected to the deformable structure and is electrically couplable to each of the electrodes;
    injecting an alternating current with a predetermined current frequency from each of a plurality of current sources through a predetermined electrode pair selected from the plurality of electrodes, wherein the frequency provided by each current source is different to the frequency provided by all other current sources,
    recording a plurality of voltages, wherein each voltage is recorded between a predetermined pair of electrodes,
    analysing the plurality of voltage recordings in combination to determine the shape of the deformable structure, and
    controlling locomotion or actuation of a soft robot according to the determination of the shape of the deformable structure.

12. The method according to claim 11,
    wherein controlling the locomotion or actuation of the soft robot comprises the steps of:
    (a) setting a goal position for the deformable structure to achieve by controlling movement of the soft robot;
    (b) evaluating the shape of the deformable structure;
    (c) initiating movement of the soft robot towards reaching that goal;
    (d) re-evaluating the shape of the deformable structure;
    (e) repeating steps b-d until the goal set in step a is achieved.

13. The method according to claim 12, wherein all of steps b-e are performed by a computer in a closed loop system.

14. The sensor system according to claim 1, wherein the soft robot is configured for minimally invasive surgery.

* * * * *